(12) United States Patent
Hegenauer

(10) Patent No.: US 6,197,813 B1
(45) Date of Patent: Mar. 6, 2001

(54) STABLE LIQUID MINERAL ASCORBATE COMPOSITIONS AND METHODS OF MANUFACTURE AND USE

(75) Inventor: John C. Hegenauer, Prescott, AZ (US)

(73) Assignee: Oxycal Laboratories, Inc., Prescott, AZ (US)

( * ) Notice: Subject to any disclaimer, the term of this patent is extended or adjusted under 35 U.S.C. 154(b) by 0 days.

(21) Appl. No.: 09/331,342
(22) PCT Filed: Feb. 5, 1999
(86) PCT No.: PCT/US99/02735
 § 371 Date: Jun. 15, 1999
 § 102(e) Date: Jun. 15, 1999
(87) PCT Pub. No.: WO99/39580
 PCT Pub. Date: Aug. 12, 1999

(30) Foreign Application Priority Data

Feb. 6, 1998 (WO) .................................. PCT/US98/02333

(51) Int. Cl.[7] .................................................. A61K 31/34
(52) U.S. Cl. ............................................. 514/474; 514/970
(58) Field of Search ..................... 424/54, 59; 514/474, 514/970

(56) References Cited

U.S. PATENT DOCUMENTS

| | | | |
|---|---|---|---|
| 5,173,214 | * | 12/1992 | Kissel ................................... 252/518 |
| 5,437,880 | * | 8/1995 | Takaichi et al. ........................ 426/73 |
| 5,658,578 | * | 8/1997 | Ogawa et al. ......................... 424/401 |
| 5,674,527 | * | 10/1997 | Inoue et al. ........................... 424/450 |
| 5,696,169 | * | 12/1997 | Otsu et al. ............................. 514/675 |
| 5,807,542 | * | 9/1998 | Challis et al. .......................... 424/59 |
| 5,906,811 | * | 5/1999 | Hersh ...................................... 424/54 |
| 5,955,083 | * | 9/1999 | Bonte et al. ....................... 424/195.1 |
| 5,968,533 | * | 10/1999 | Porter et al. .......................... 424/401 |

FOREIGN PATENT DOCUMENTS 62-70309 * 3/1987 (JP) .

* cited by examiner

Primary Examiner—S. Mark Clardy
(74) Attorney, Agent, or Firm—Drummond & Duckworth

(57) ABSTRACT

Liquid vitamin C concentrate compositions comprise a mineral ascorbate and a pharmacologically acceptable liquid organic polyol solvent for the mineral ascorbate, the concentrate having a pH between about 5 and 7. The concentrate may also contain an aldonic compound and/or a pharmacologically acceptable zinc compound. The concentrate compositions are prepared by heating the solvent to 50–90° C. and mixing the ascorbate and/or aldonic compound and/or zinc compound into the heated solvent, preferably in the absence of oxygen. These concentrate compositions are also characterized as a composition which comprises the reaction product of a mineral ascorbate and a pharmacologically acceptable liquid organic polyol solvent and, optionally an aldonic compound and/or a soluble non-toxic zinc compound, which reaction product includes 4-hydroxy-5-methyl-3(2H)-furanone and/or 3-hydroxy kojic acid.

Finished vitamin C products, characterized by excellent long term vitamin C stability, are conveniently prepared by incorporating the concentrates into finished cosmetic, medical and food products.

16 Claims, 10 Drawing Sheets

STABLE LIQUID MINERAL ASCORBATE COMPOSITIONS AND METHODS OF MANUFACTURE AND USE

FIELD OF THE INVENTION

This invention relates to stable vitamin C concentrate compositions for preparing finished products such as cosmetic and dermatologic preparations, food products, e.g., processed foods, beverages, and nutritional supplements, and medicinal, dental, opthalmic and surgical compositions for both enteral and parenteral introduction.

In another respect, the invention concerns finished products prepared from such concentrate compositions.

Another aspect of the invention pertains to methods of manufacturing such concentrate compositions and finished products.

In yet another respect, the invention relates to methods of using such finished products.

BACKGROUND OF THE INVENTION

Vitamin C has many known biological functions, e.g., acting as a wound healing accelerant. to prevent or treat periodontal disease, as an enzymatic co-factor, as a "sparing" agent against vitamin E depletion, as a collagen-synthesis stimulator, etc. Vitamin C is known to counteract oxygen-containing free radicals, including both the superoxide and hydroxyl radicals. These oxidative free radicals are generated in-vivo under a variety of normal and pathological conditions, and vitamin C is known for its ability to ameliorate conditions caused by oxygen free radicals, e.g., sunburn, cataracts, premature aging and a variety of other degenerative conditions.

Because of the beneficial effects attributed to vitamin C, many attempts have been made to formulate liquid vitamin C compositions. However, because of its notorious instability, particularly at higher pH's, pharmacologists and other scientists working in the field have had difficulty formulating stable liquid vitamin C compositions that would be useful in preparing various end-use products.

It would be highly desirable to provide vitamin C concentrate compositions, and end-use products prepared from these concentrates, which have improved physical stability and chemical stability under less acidic conditions.

It would also be highly desirable to provide such vitamin C concentrate compositions which are especially adapted for use in preparing a wide variety of end-use products, including cosmetic products, medical products, including dermatologic, dental, opthalmic and surgical products, wound healants, etc., and various food products, e.g., processed foods, beverages, nutritional supplements, etc.

PRIOR ART

U.S. Pat. No. 2,822,317 (Gulesich et al.) discloses a liquid aqueous composition which includes L-ascorbic acid (including ascorbyl fatty acid esters), a ferrous salt (including ferrous sulfate, lactate, gluconate, succinate, glutamate and choline citrate salts and complex salts) and a $C_5$–$C_6$ polyhydric alcohol. This composition is said to have "satisfactory" stability at pH=2.0 to 3.5.

U.S. Pat. No. 5,587,149 (Punto et al.) discloses that solutions of ascorbic acid dissolved in polyethylene glycol ("PEG") and then emulsified in a silicone fluid to form an (ascorbic acid+PEG)-in-silicone emulsion are physically "stable", in the sense that they "do not exhibit creaming, sedimentation, or phase separation." However, to prevent chemical degradation of the ascorbic acid, these emulsions are encapsulated in gelatin "twist-off" capsules.

U.S. Pat. No. 4,938,969 (Schinitsky et al.) discloses a composition of ascorbic acid, tyrosine and a water-soluble zinc salt, e.g., zinc sulfate, in "a tissue compatible vehicle" (e.g., mineral oil+sesame oil+glycerine+PEG), but does not report the chemical or physical stability of this composition.

U.S. Pat. No. 5,536,500 (Galey et al.) reviews several stabilization methods for vitamin C, involving physical techniques (e.g., incorporation in zeolites, etc.), chemical modification of the ascorbic acid molecule, such as conversion to the phosphodiester in combination with vitamin E, and functionalization of the enediol group by formation of phosphate, sulfate, ether or ester functions. Ascorbyl esters of cinnamic acid are disclosed, but neither the physical or chemical stability of such esters in liquid carriers is reported.

U.S. Pat. No. 5,140,043 (Darr et al.) discloses topical compositions of ascorbic acid (or a reducing analog), in a water-(glycol or polyol) carrier. It is asserted that the 12-week shelf stability is acceptable ($\approx$100% ascorbic acid retention) only if the ratio of water to glycol/polyol carrier is high (e.g., at least 1:1) and the pH is maintained at $\leq 3.5$.

U.S. Pat. No. 5,350,773 (Schweikert et al.) reports liquid compositions containing a fat-soluble substance are stabilized against "microbiological spoilage" for as long as six months, by dispersing the fat-soluble substance in a glycerol or glycerol-water continuous phase containing an ascorbyl fatty acid ester (e.g., ascorbyl palmitate) "emulsifier."

U.S. Pat. No. 5,736,567 (Cantin et al.) discloses aqueous ascorbic acid-polyol-oil compositions, with relatively lower water contents than conventional cosmetic or dermatologic compositions.

DESCRIPTION OF THE INVENTION

BRIEF STATEMENT OF THE INVENTION

I have now discovered liquid Vitamin C concentrate compositions having improved stability, which are especially adapted for preparing finished products. These concentrate compositions include at least one mineral ascorbate, dissolved in at least one pharmacologically acceptable liquid organic polyol solvent for the mineral ascorbate(s). The concentrate compositions have a pH of at least about 5, preferably from about 5 to about 7.

According to another aspect of the invention, the concentrate composition preferably also contains at least one aldonic compound.

In yet another aspect, the concentrate composition of the invention preferably also includes a pharmacologically acceptable zinc compound, preferably a water-soluble zinc salt.

The invention also comprises a liquid vitamin C composition which includes the reaction product of at least one mineral ascorbate and at least one pharmacologically acceptable liquid polyol solvent for the mineral ascorbate.

The invention further includes liquid vitamin C compositions which include 4-hydroxy-5-methyl-3(2H)-furanone and/or 3-hydroxy-kojic acid, as well as such compositions which also include at least one aldonic compound and/or a pharmacologically acceptable zinc compound.

The invention also contemplates finished products prepared from the concentrate compositions and/or reaction products defined above.

According to another aspect of the invention, finished emulsion products comprise a continuous phase and a disperse phase, the concentrate composition being carried in one of these phases.

In still another respect, the invention includes methods for administering vitamin C which include the step of topically, orally, enterally or parenterally introducing to humans or animals, a finished product prepared from the above-defined concentrate composition.

According to yet another embodiment, the concentrate compositions/reaction products defined above include a compound which is characterized by the 285 nm high-performance liquid chromatographic (HPLC) peak which appears after the solvent front peaks and before the ascorbate peak, now identified as 4-hydroxy-5-methyl-3(2H)-furanone, i.e,

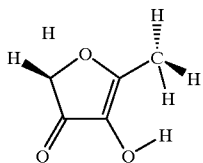

4-hydroxy-5-methyl-3(2H)-furanone and such compositions and reaction products which also include 3-hydroxy-kojic acid, i.e.,.

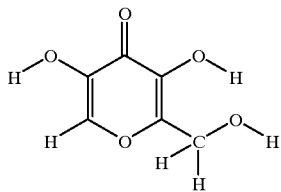

3-hydroxy-kojic acid

Other aspects and features of the invention will become apparent to those skilled in the art from the following detailed description thereof, taken in conjunction with the drawings.

DEFINITIONS

Figure 1A:
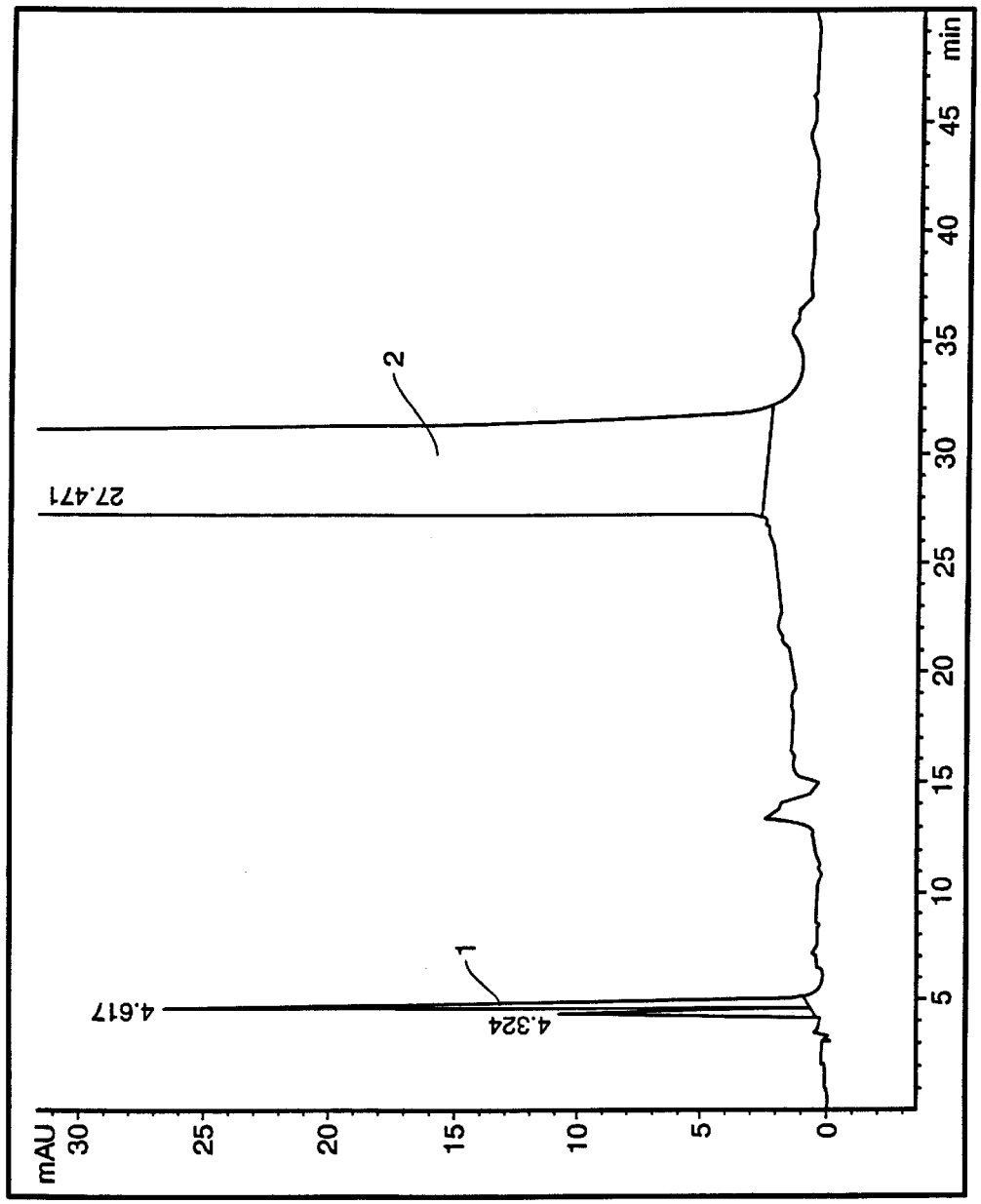
FIG. 1a is an HPLC chromatogram representing the major components of a typical prior-art composition prepared in accordance with U.S. Pat. No. 5,140,043 to Darr et al.

As used herein, the following terms have the meanings indicated:

"Mineral ascorbate" means a pharmacologically acceptable salt of ascorbic acid, including salts and complexes of ascorbate anions with pharmacologically acceptable cations of the alkali elements (sodium, potassium, etc.), alkaline-earth elements (calcium, magnesium, etc.), or transition elements (copper, iron, zinc, chromium, etc.).

"Liquid" includes lotions and viscous creams which conform to the shape of the container in which they are placed, as well as self-supporting gels, pastes and the like.

"Aldonic" component means an aldonic acid, the simplest of which is glyceric acid, the non-toxic salts thereof (e.g., sodium, potassium, calcium, etc.) and open-chain and cyclic condensation products thereof, namely, open-chain aldonic esters, aldono-lactones and aldono-lactides.

"pH" of the concentrate compositions of the invention is the pH determined potentiometrically by diluting one part of the subject liquid with 10 parts of water, as described in U.S. Pharmacopeia XXIII ["The U.S. Pharmacopeia/The National Formulary (USP 23/NF 18)", United States Pharmocopeial Convention, Inc., 12601 Twinbrook Parkway, Rockville, Md. 20852 USA (1995).]

"Stability" refers to the ability of a composition to retain at least 90% of its nutritional or pharmaceutical potency (ascorbate content), as determined at room temperature (22° C.), or at an elevated temperature and converted to room temperature based on the Arrhenius equation, which relates the rate constant of a chemical reaction to the energy of activation and absolute temperature.

DETAILED DESCRIPTION OF THE INVENTION

The concentrate compositions of the invention are adapted to be converted by further processing steps to a wide variety of end-use products having various consistencies from runny liquids to viscous creamy lotions to self-supporting pastes and gels, and even semi-solid sticks, etc., depending on the other components with which the concentrate is mixed.

Although the concentrates are initially formulated as an easily handled "syrup", it is also contemplated that the concentrates can be further formulated into an intermediate emulsion "cream". The "cream" form of the concentrate can, in turn, be conveniently incorporated into existing emulsion bases—bases which are commonly used in various finished end-use products, e.g., cosmetics, dermatologic preparations, etc.—without major revision of the end-product manufacturer's processing procedures and equipment.

The mineral ascorbates used in practicing the invention are conveniently available as high-purity commercial products. If a single mineral ascorbate is used, it is presently preferred to use calcium ascorbate, although it is contemplated that two or even more mineral ascorbates may be employed, depending upon the end-use product involved. The concentration of the mineral ascorbate can range from less than 1 to upwards of 80 wt. % of the syrup concentrate product, which will vary with the desired viscosity of the syrup and the solubility of the mineral ascorbate(s) employed in the solvents or solvent mixtures employed. For example the solubility of calcium ascorbate dihydrate in various polyols varies from less than one wt. % in pure butanediol or certain pure polyethylene glycols, to 40–50 wt. % in pure glycerol, to 50–60 wt. % in 70% sorbitol and 75–80% in 70% polyethylene glycol of low molecular weight. For comparison, the solubility of sodium ascorbate varies from practically zero in pure butanediol and pure polyethylene glycol to 15–20 wt. % in 100% glycerol and 30–35 wt. % in 70% sorbitol.

Although calcium ascorbate is presently preferred, depending on the end-use of the finished products, other pharmacologically acceptable mineral ascorbates, illustratively, magnesium, sodium, potassium and/or zinc ascorbates and mixtures thereof are effectively employed.

The aldonic compound can be obtained from commercial suppliers, e.g., high-purity calcium threonate is available as L-threonic acid hemi-calcium salt, manufactured by Farmak Olomouc, distributed by Helm New York, Piscataway, N.J. Alternatively, and preferably, the aldonic component is derived from products manufactured under U.S. Pat. Nos. 4,822,816; 4,968,716 and 5,070,085 to Markham and corresponding foreign patents. These combination mineral ascorbate-aldonic compositions are internationally available under the trademark Ester-C® brand mineral ascorbates from Inter-Cal Corporation of Prescott, Ariz., U.S.A. If these combination mineral-aldonic compositions are employed, the weight ratio of mineral ascorbate to aldonic compound is about 99:1, or approximately 80:1 weight ratio of ascorbate moiety to aldonic moiety. If a separate source of the aldonic compound, e.g., calcium threonate, is employed as the aldonic component, I prefer to employ it in approximately the same weight ratio of ascorbate moiety to aldonic moiety as that achievable by use of Ester C® mineral ascorbates, namely 80:1 weight ratio. Higher weight ratios, leading to lower absolute concentration of the aldonic moiety, are at least partially effective. Lower weight ratios, leading to higher absolute concentrations of the aldonic moiety, are not harmful, but are limited by the lower solubility of the calcium salts of the aldonic components in polyol media. The aldonic component potentiates the topical, enteral and parenteral efficacy of the mineral ascorbates in end-use products prepared from the liquid compositions of the invention, as in the potentiation of the enteral efficacy of various vitamin C-aldonic compositions, as disclosed by the above-cited Markham patents.

The organic polyol solvents employed in practicing my invention are chosen for pharmaceutical acceptability, their ability to solublize the mineral ascorbate, the aldonic components and the optional zinc components of the concentrate, water content and effect on the stability of the ascorbate component. At present I prefer to employ mixtures of commercially available glycerol which generally contains 5% or less water and commercially available sorbitol, which is a saturated (70%) solution in water. In general, I prefer to minimize the water content of the solvent(s), consistent with economic and functional considerations. Although mixtures of commercially available glycerol and sorbitol are not completely water-free, the chemical activity of the water is reduced by the high concentration of the other solutes, by hydrogen bonding with the hydroxyl groups of the solvents and/or coordinated to the cations of the mineral ascorbate(s) and other solutes. Other polyols which can be employed include propylene glycol, hexylene glycol, butylene glycol and the almost infinite molecular weight range of polyethylene glycols, as well as so-called sugar alcohols, e.g., xylitol, and mixtures thereof with other polyols.

These concentrates can be prepared entirely with one solvent, e.g., glycerol or sorbitol, or mixtures of solvents. The final choice of solvent will depend on economics and other relevant factors. The stability of the vitamin C is somewhat better in the sorbitol solvent than in pure glycerol. Propylene glycol is the least desirable from the standpoint of vitamin C stability, although other factors, e.g., skin-penetration adjuvant effect, may dictate using at least some of this solvent in combination with other polyols.

If a zinc compound is incorporated into the concentrates of the invention, I presently prefer to employ an amount of zinc compound such that the weight ratio of the mineral ascorbate to the zinc compound is approximately 40:1, although, again, somewhat lower ratios are not harmful and higher ratios are at least partially effective. The zinc compound can be furnished as commercially available high-purity, pharmaceutically acceptable zinc salts, at present preferably zinc acetate dihydrate. Alternatively, the zinc component of these concentrates can be provided as zinc ascorbate, either alone or in combination with aldonic components, e.g., threonates, as in the Ester-C® brand mineral ascorbate products available from Inter-Cal Corporation of Prescott, Ariz., U.S.A. If one employs zinc ascorbate as the source of zinc, then one can adjust the amounts of other mineral ascorbate(s) employed to account for the conjoint contribution of ascorbate from the zinc ascorbate. An enormous body of biomedical literature discloses the therapeutic effects of topically applied zinc for wound healing, burn treatment and connective tissue repair and much of this literature recognizes the synergistic effects of zinc and vitamin C. Aside from the similar enteral and parenteral effects of the combination of vitamin C and zinc in products which are prepared from the concentrates of the present invention, the presence of zinc in the concentrate compositions also enhances the production of a unique component of the concentrates, which is identified by the HPLC techniques described below.

The procedures for preparing the concentrate compositions of the invention are not highly critical and various modifications of the procedures described below will readily occur to persons skilled in the art having regard for these disclosures. In general the dry components, namely mineral ascorbate and, optionally, the zinc compound and/or aldonic compound, are separately mixed with the solvent which has been preheated to the range 70–90° C., preferably 50–90° C. The suspension of each component is stirred until it is completely dissolved. Upon cooling the product is a viscous. but pourable, i.e., "syrupy", liquid which may vary in color from light-yellow to honey-colored.

According to the presently preferred embodiment of the invention, the viscosity of the finished concentrate product can be lowered and shelf stability of the color of the concentrate product, which may tend to darken with storage, can be improved by first heating the solvent in a stirred, steam-heated, jacketed kettle, to only about 50–90° C., dissolving the aldonic and any optional zinc components into the heated solvent and then ceasing external heating while dissolving the remaining components in the solvent-aldonic solution. The final temperature of the concentrate product after dissolving all of the components will rise and, desirably will not exceed approximately 60°C.

To further improve the Vitamin C shelf stability of the concentrate product, all mixing of the components is preferably carried out in the absence of oxygen, under a blanket of an oxygen-free inert gas, such as nitrogen or carbon dioxide. This can be accomplished by bubbling the intert gas into a covered, vented mixing kettle, thereby excluding air from the kettle. Otherwise cavitation of the mixer impeller tends to introduce air into the mixture, thereby inducing oxidation of the components during the mixing operations. According to this preferred embodiment, accelerated aging tests (described below) indicate that the various concentrate product compositions of the invention will retain greater than 95% of their original vitamin C potency for 25 months at room temperature.

To prepare emulsions from these concentrates, one phase is prepared by mixing the concentrate with components which typically include waxes, oils, bases, preservatives, and emulsifiers at an elevated temperature, e.g., 70° C. (or a temperature below the thermal decomposition temperatures of the oil phase components and the mineral ascorbates). An aqueous phase is prepared which may contain preservatives, color and/or fragrances and/or flavoring agents in distilled water and heated to the same approximate elevated temperature, e.g., 70° C. The heated oil phase is placed in a stirred mixing vessel and concentrate is blended into it to form a fine emulsion. The aqueous phase is then slowly added with stirring and mixing is continued for several minutes. The hot emulsion (normally thick, but pourable with difficulty) is then transferred into packaging containers.

Alternatively, the concentrate compositions of the invention can be incorporated into the aqueous phase of an emulsion by techniques which are well-known in the art, or additional polyol-soluble or suspendible components (biologically or medicinally active ingredients, preservatives, flavors, fragrances, etc.) can be dissolved or suspended directly into the concentrates to form the finished products by art-recognized techniques.

WORKING EXAMPLES

The following examples are presented to aid in understanding the invention and to illustrate the presently preferred practice thereof. As illustrations they are not intended to limit the scope of the invention, which is defined only by the appended claims.

Example 1

This example illustrates the preparation of a typical "syrup" concentrate of the invention.

119.05 g of 70% sorbitol solution is heated to 70–90° C. 0.57 g of calcium threonate is added and the suspension is stirred until the threonate is completely dissolved. 3.32 g of zinc acetate dihydrate is added to the hot threonate solution and the mixture is stirred until the zinc acetate is completely dissolved. 119.05 g of 100% glycerol is added and the mixture is heated to 50–90° C. 48.20 g of calcium ascorbate dihydrate is added to the hot sorbitol/glycerol solution and stirring is continued until it is completely dissolved. A viscous solution results, which upon cooling yields a viscous but pourable light-yellow syrupy liquid. The pH of the resulting concentrate is 6.65. The composition of this concentrate, excluding anions other than ascorbate, is

| Vitamin C | 13.64 wt. % |
| Calcium | 1.59 |
| Zinc | 0.34 |
| Threonic acid | 0.17 |
| Polyols (minus water) | 69.74 |
| Water (total) | 13.90 |

Example 1a

This example illustrates the preparation on a concentrate product of the invention containing sodium ascorbate.

842.2 g of 70% sorbitol solution is heated to 60° C. 2.00 g of calcium threonate is added and the suspension is stirred until the threonate is completely dissolved. 154.80 g of sodium ascorbate is added to the hot sorbitol solution, and stirring is continued until it is completely dissolved. Upon cooling, a viscous, but pourable pale-yellow liquid product is obtained.

The composition of the liquid concentrate product is, excluding cations other than sodium:

| Vitamin C | 13.7 wt % |
| Sodium | 1.8 |
| Threonic acid | 0.17 |
| Polyols (minus water) | 59.01 |
| Water (total) | 25.29 |

This concentrate product has Vitamin C stability comparable to the product of Example 1, is lighter in color, has improved color stability, and is less viscous.

Example 2

This example illustrates the preparation of a finished cosmetic cream or topical product from the concentrate of Example 1. (All concentrations are in wt. %.)

| Phase I (aqueous) | |
| --- | --- |
| Water (deionized) | 67.52 |
| Imidazolidinyl urea | 0.20 |
| Coloring & Fragrance (optional) | 0.51 |
| Phase II (oil) | |
| Mineral Oil | 5.04 |
| Petrolatum | 0.52 |
| Lanolin | 0.55 |
| Cetyl alcohol | 1.12 |
| Stearyl alcohol | 0.70 |
| Stearic acid | 1.60 |
| Triethanolamine | 0.24 |
| Isopropyl myristate | 1.38 |
| Glyceryl monostearate | 4.12 |
| Squalene | 0.72 |
| Silicone oils | 1.13 |
| Beeswax | 0.62 |
| Sorbitan monostearate (Span 60) | 0.54 |
| Polyoxyethylene sorbitan monostearate (Tween 61) | 0.66 |
| Polyoxyethylene 20 cetyl ether (Brij 58) | 0.96 |
| Polyoxyethylene 40 stearate (Myrj 52) | 1.34 |
| Caprylic/capric triglycerides | 1.44 |
| Triglycerides (olive oil) | 1.51 |
| Propyl parahydroxybenzoate | 0.12 |
| Methyl parahydroxybenzoate | 0.17 |
| Vitamin C Concentrate (Example 1) | 7.29 |

The components of Phase I are dissolved and Phase I is heated to 70° C. The components of Phase II are melted together by heating them to 70° C., adding the Vitamin C concentrate as the final component. Phase II is stirred with a rotary mixer while Phase I is poured in as a thin stream. The combined phases are stirred until the mixture cools to about 45–50° C., and the cream product is transferred to containers.

When the oil phase containing the syrupy concentrate of Example I is combined with the water phase to prepare the final product formulation (at approx. 7.3 wt. % concentrate), a pleasing creamy emulsion results, which has excellent vitamin C stability and excellent humectant and emollient characteristics due to the polyols in the concentrate. The final composition of such an emulsified product is

| | |
|---|---|
| Vitamin C | 1.00 wt. % |
| Calcium | 0.12 |
| Zinc | 0.025 |
| Threonic Acid | 0.013 |
| Polyols (minus water) | 5.11 |

The pH of the final emulsified product is 5.3 and may be made less acidic, e.g., by inclusion of a higher concentration of triethanolamine.

Example 2a

This example illustrates the preparation of a food product, using the concentrate product of the invention, e.g., the concentrate compositions of Examples 1 or 1a.

500 ml of dry granulated sugar is added to 125 ml of water and 125 ml of corn syrup and the mixture is stirred and brought to boil at 150° C. Heating is discontinued and cherry flavoring is added to taste and desired color. The concentrate product of Example 1 is added in the quantity required to obtain the desired Vitamin C content, e.g., 30 mg Vitamin C/g of "candy" food product. The concentrate and the sugar-syrup base are thoroughly mixed for sufficient time to fully disperse the concentrate product. Portions of the resulting hot concentrate-syrup mixture are transferred to the cavities a candy mold and cooled to form a Vitamin C enriched hard candy product.

Example 3

This example illustrates the HPLC procedure for characterizing the concentrate products of the invention and for comparing these concentrate compositions with the prior art.

High Performance Liquid Chromatography (HPLC) is carried out using a Hewlett-Packard Model 1050 instrument equipped with a diode array detector. Phenomenex "Luna 2" reversed-phase 5-micron C-18 chromatographic columns are used (4.6×250 mm separation column; 4.6×30 mm guard column). The mobile phase is 0.2% (v/v) dicyclohexylamine adjusted to pH 5.3 with o-phosphoric acid. All solutions are filtered through a 0.2-micron nylon filter before use. To facilitate comparisons, samples for chromatography are adjusted to a final concentration of approximately 0.3% (w/v) ascorbate by dilution in the mobile phase (described above), and 100 microliters is injected into the column. Isocratic elution is carried out with the same mobile phase. Wavelength detection using the diode array detector spans 200 to 360 nm. 2-dimensional HPLC chromatograms display column retention time (minutes) on the x-axis and detector response at 200 nm (absorbance) on the y-axis. 3-dimensional HPLC chromatograms display column retention time (minutes) on the x-axis, the absorbance (in arbitrary detector response units) on the y-axis and the wavelength of light scanned by the diode array detector (nm) on the z-axis.

Example 4

This example illustrates the preparation of a vitamin C product as disclosed in U.S. Pat. No. 5,140,043 (Darr et al.) and a comparative control without vitamin C.

Sample Preparation: 10.0 g of ascorbic acid is transferred to a 100-ml volumetric flask. 80.0 ml of deionized water is added and the material is dissolved. Propylene glycol is added to bring the final volume to 100 ml.

Control Preparation: 80.0 ml of deionized water is added to a 100 ml volumetric flask. Propylene glycol is added to bring the final volume to 100 ml.

HPLC Procedure: 7.5 g of the above sample and control preparations are transferred to 100 ml volumetric flasks. The flasks are brought to volume with deionized water and the material is thoroughly dissolved and mixed well. 4.0 ml of each of these solutions are transferred to separate 10 ml flasks, which are brought to volume with the HPLC mobile phase. The samples are filtered through a 0.2-micron filter and 100 microliters of each are injected. The resulting chromatogram are depicted in FIG. 1a (test) and FIG. 1b (control).

Example 5

This example illustrates the preparation of a vitamin C product as disclosed in U.S. Pat. No. 4,983,382 and a comparative control prepared without vitamin C.

Sample preparation: 5.0 g of ascorbic acid, 10.0 g of deionized water, 21 g of propylene glycol and 61.1 g of ethanol are transferred to a 100 ml flask. The flask is placed in a sonicator and the ascorbic acid is observed to completely dissolve.

Control preparation: 10.0 g of deionized water, 21 g of propylene glycol and 61.1 g of ethanol is transferred to a 100.0 ml flask. The flask is placed in a sonicator and thoroughly mixed.

DETAILED DESCRIPTION OF THE DRAWINGS

Figure 1B:
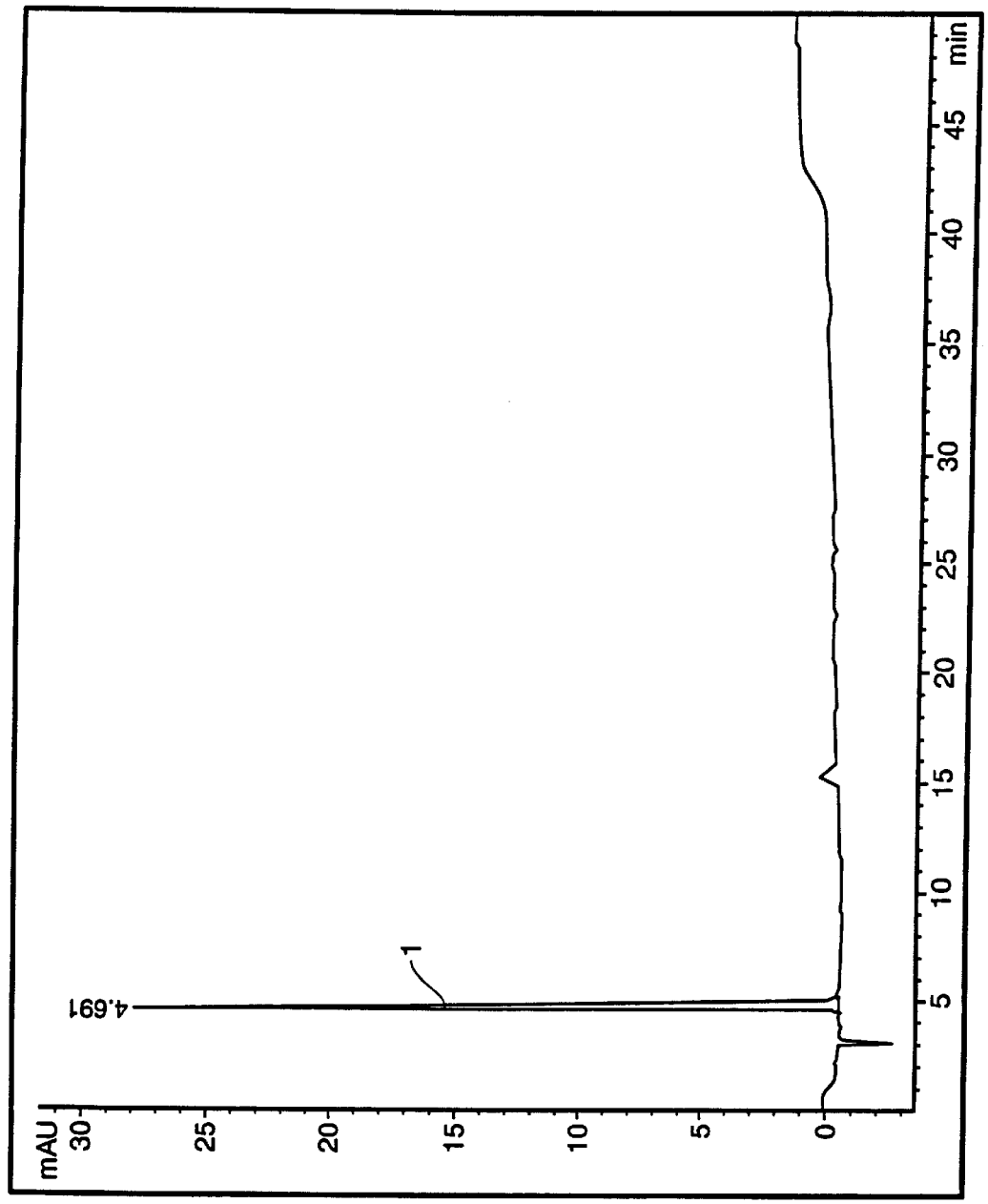
FIG. 1b is a chromatogram representing a control composition which includes the same components minus ascorbic acid.

FIGS. 1a and 1b illustrate that a typical liquid ascorbic acid solution product of the prior art does not contain any major components other than those in the solvent front 1 and the intact ascorbic acid components 2. As shown, the peaks of FIG. 1a are identical to the control shown in FIG. 1b, except for the ascorbic acid peak 2 at 26–30 minutes retention time, and the peak at 4.3 minutes which is a solvent perturbation peak.

Figure 2A:
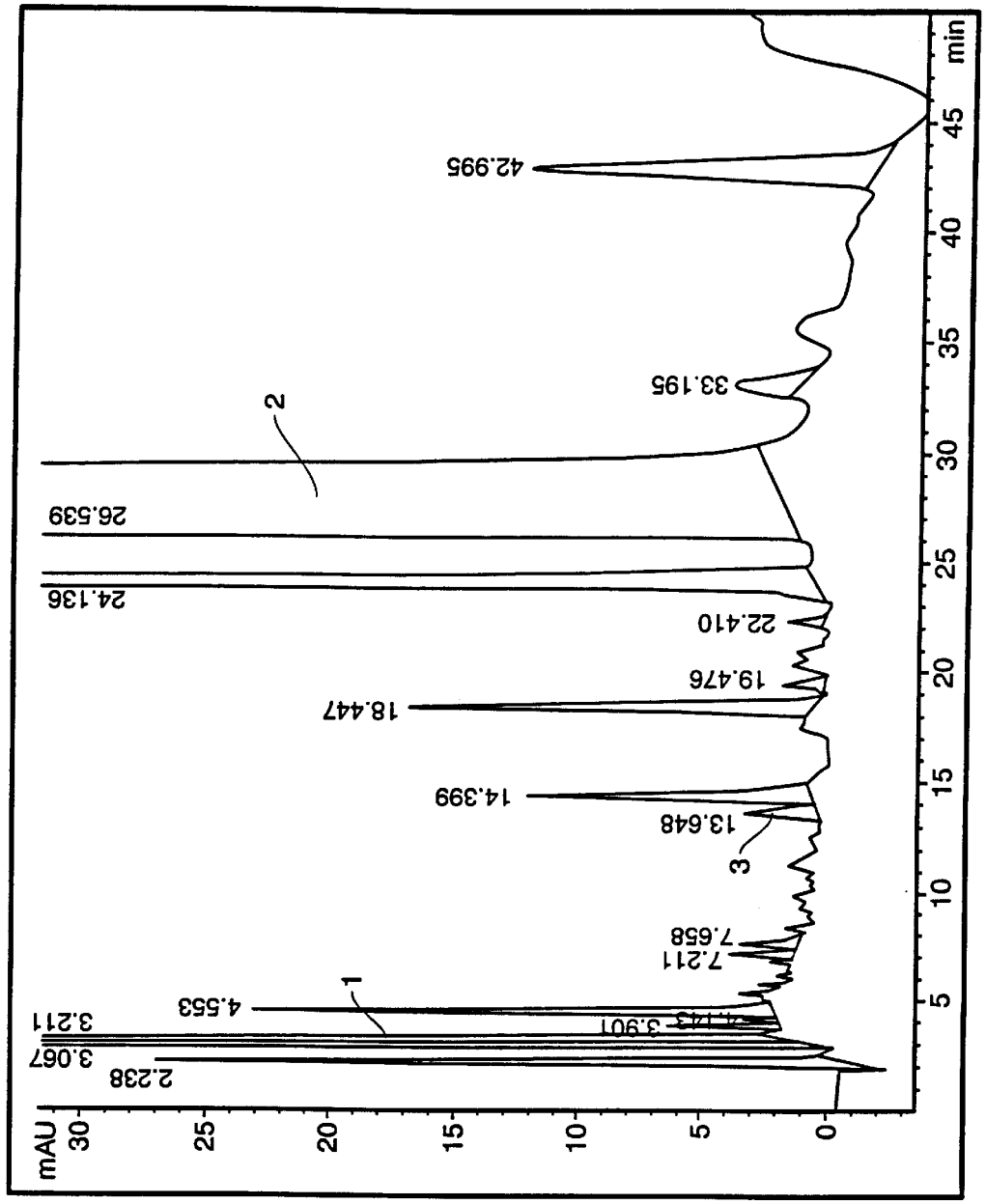
FIG. 2a is an HPLC chromatogram representing the major components of a vitamin C concentrate composition of the present invention which includes a zinc compound.
Figure 2B:
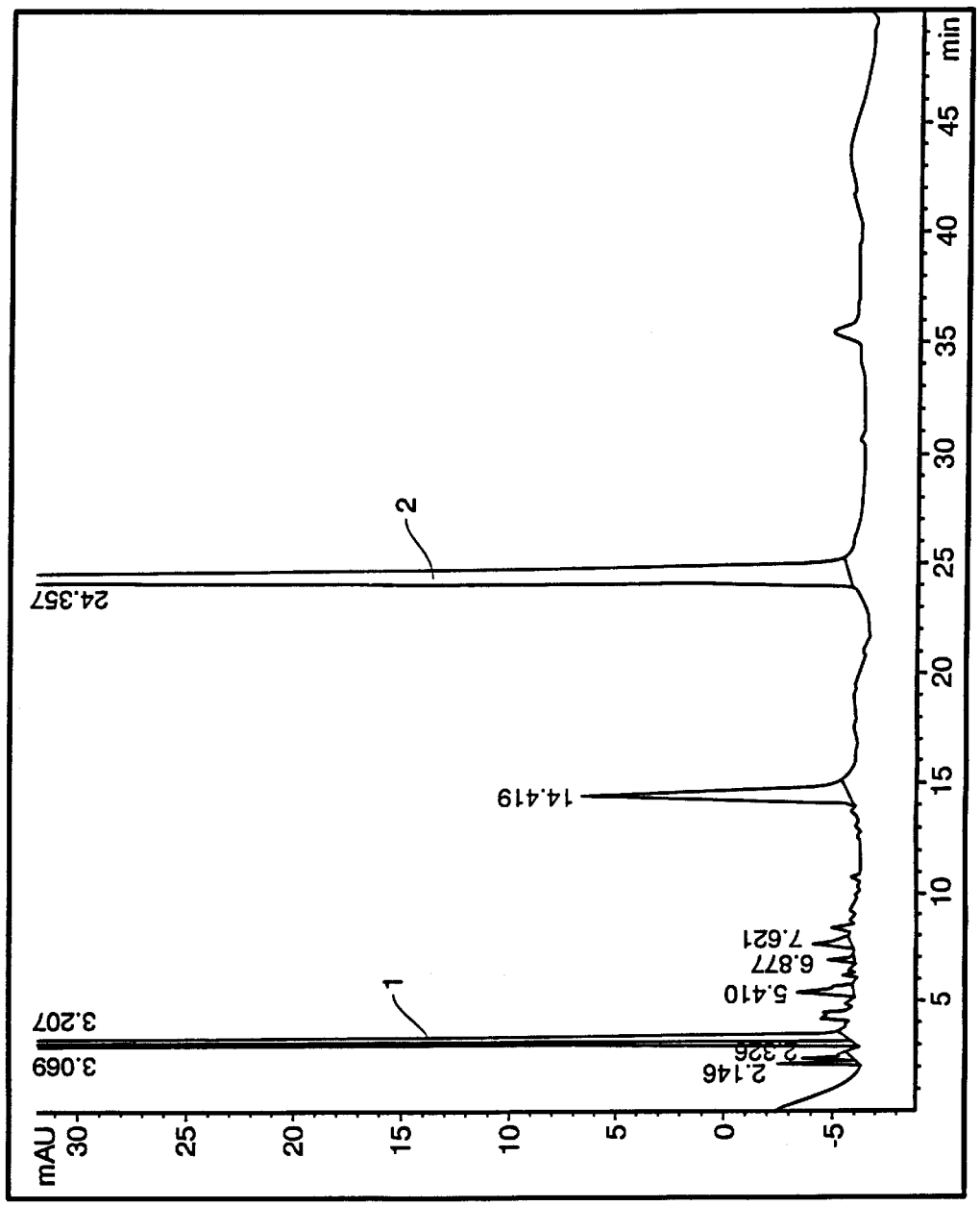
FIG. 2b represents a control composition which includes the same components except for the mineral ascorbate.
Figure 3A:
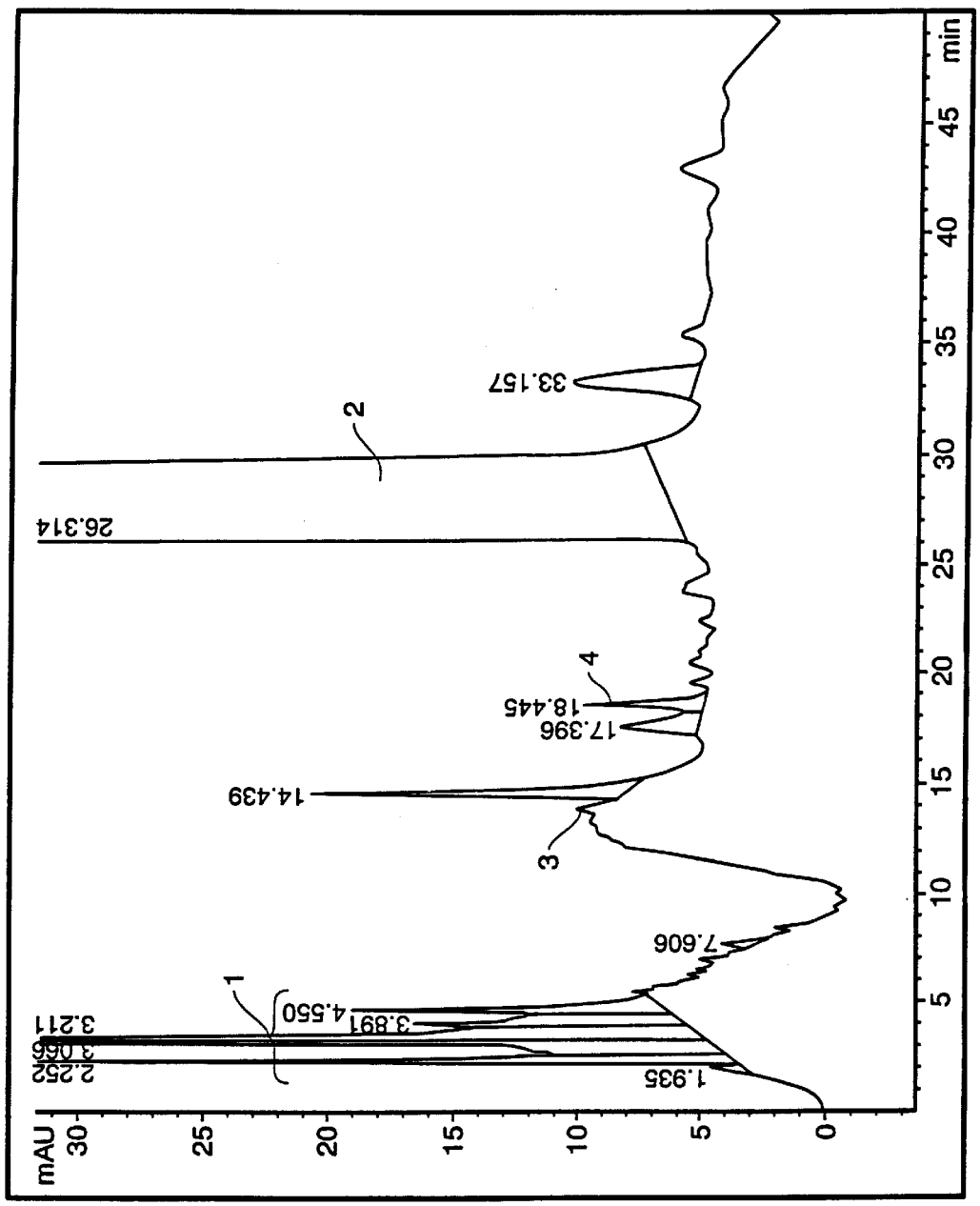
FIG. 3a is an HPLC chromatogram representing the major components of a concentrate composition of the present invention which does not include a zinc compound and FIG. 3b represents a control composition which includes the same components except for the mineral ascorbate.
Figure 3B:
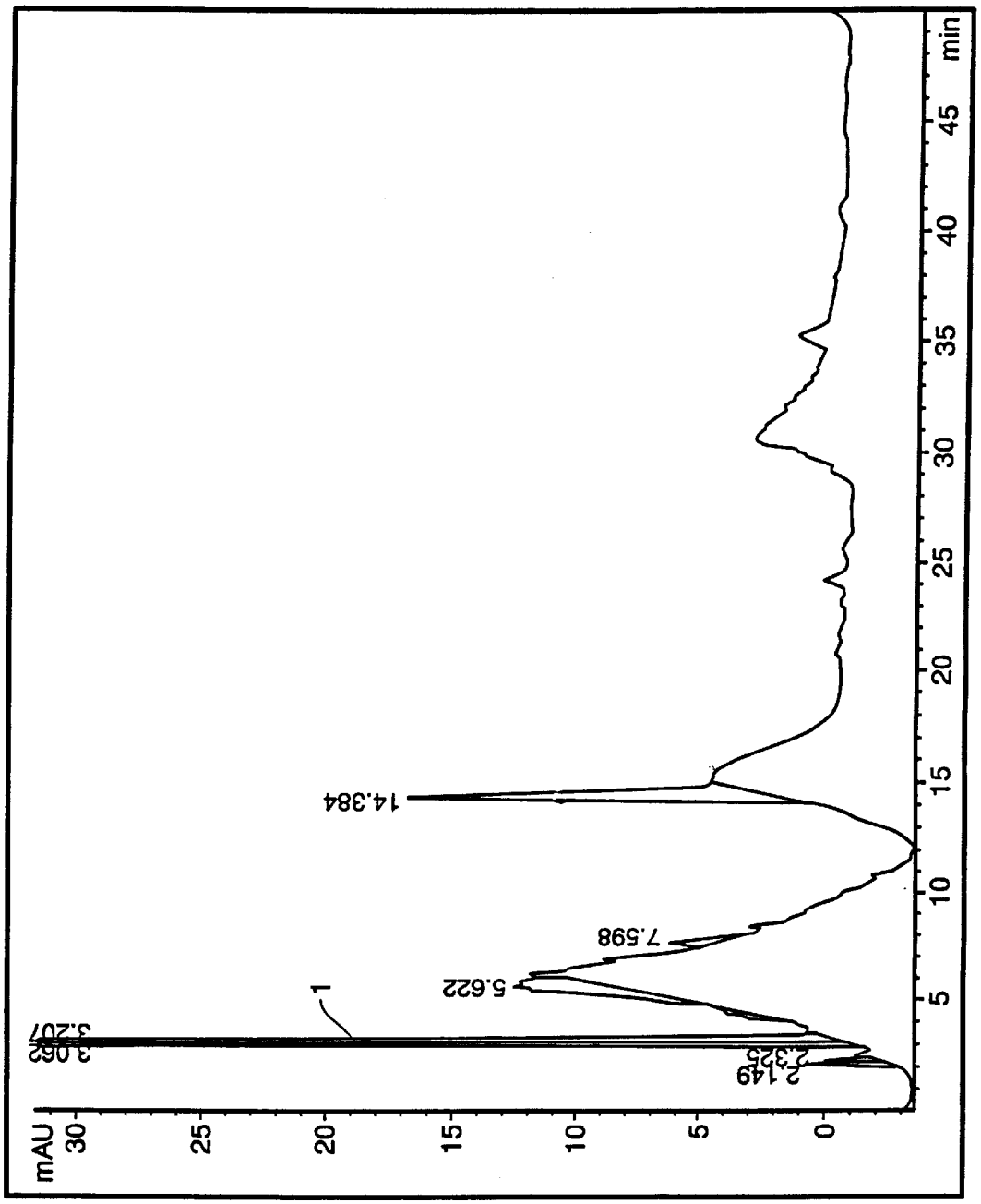

HPLC chromatograms of typical concentrate compositions of the invention, prepared with and without a zinc component, but without added threonate, are shown in FIGS. 2 and 3, respectively. FIGS. 2a and 3a are test preparations containing ascorbate; FIGS. 2b and 3b are control preparations without ascorbate. As will be apparent, there is a major peak 3 representing a compound which appears between the solvent front peaks 1 (2–3 minutes retention time) and both the threonate peak 4 (~18 minutes retention time) and the ascorbate peaks 2 (26–32 minutes retention time) in both FIGS. 2a and 3a, which does not appear in their respective control chromatograms, FIGS. 2b and 3b. This establishes that the compound represented by the non-ascorbate peak 3 in both instances was due to the presence of the ascorbate-aldonic components of the compositions and that the presence of zinc favors the production of the compound characterized by this non-ascorbate peak 3. Note that threonate is formed during the preparation of a typical concentrate, even though it is not deliberately added as a starting raw material component.

Figure 4A:
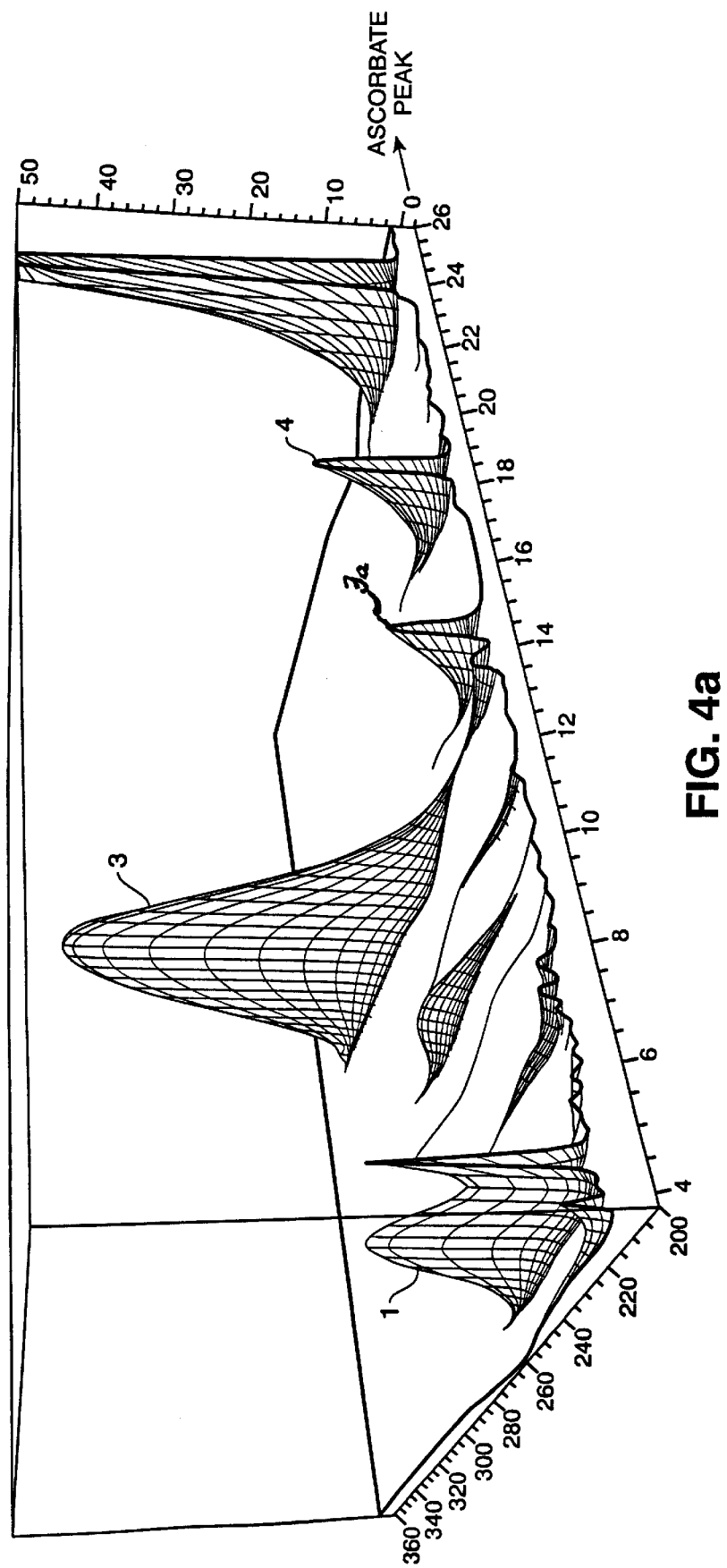
FIGS. 4a and 4b are three-dimensional HPLC charts representing the major components of concentrate compositions such as those typified in FIG. 2a and 3a, wherein the x-axis represents the retention time (minutes), the y-axis represents the absorbance (in arbitrary detector response units) and the z-axis represents the wavelength of light scanned by the diode array detector (nm)
Figure 4B:
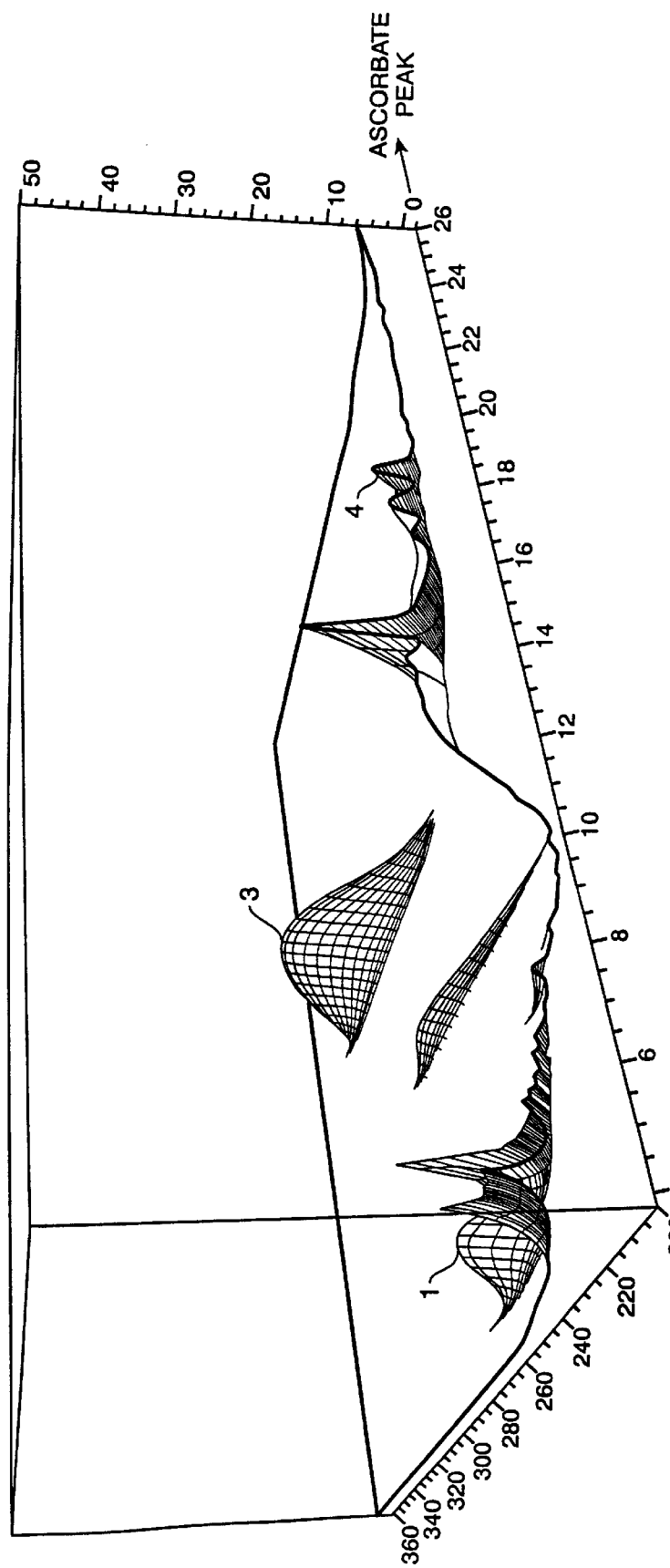

FIGS. 4a and 4b are three-dimensional HPLC chromatograms collected with the use of the diode-array detector, which more clearly depicts the peak 3 which is characteristic of the compound appearing between the solvent front peaks 1 and both the ascorbate peak 2 and the threonate peak 4. In these chromatograms, retention time forms the x-axis (left-right), detector response (absorbance, or the absorption of light) forms the y-axis (vertical), and the detector wavelength forms the z-axis (front-back). FIGS. 4a and 4b are produced using the same chromatographic data as that used in FIGS. 2a and 3a, respectively, except that the elution profile is truncated at approximately 26 minutes prior to elution of the large ascorbate peak in order to clarify the positions of other compounds formed during preparation of the concentrate compositions. The peak 3 appears in FIGS. 4a and 4b, between approximately 13–14 minutes retention time, and has an absorption maximum at approximately 285 nm. This peak, while prominent at approximately 285 nm, shows little absorbance at 200 nm, which is the wavelength commonly used in routine HPLC chromatographic detection. The compound represented by peak 3 is 4-hydroxy-5-methyl-3(2H)-furanone. This furanone derivative is present in the concentrate products of the present invention in an amount of from about 0.001 wt. % to upwards of about 0.1 wt. % or more.

The concentrate compositions of the invention also contain 3-hydroxy kojic acid, the compound, represented by the peak 3a of FIG. 4a. This kojic acid derivative is a known skin-whitening agent. According to my present information, it appears that this kojic acid derivative is present in the concentrate products of the present invention in an amount of from about 0.001 wt. % to upwards of about 0.1 wt. % or more.

The furanone and kojic acid derivatives identified above are present in the concentrate compositions of the invention, whether or not an aldonic compound has been added to the reaction mixture from which these concentrate compositions are obtained.

Figure 5A:
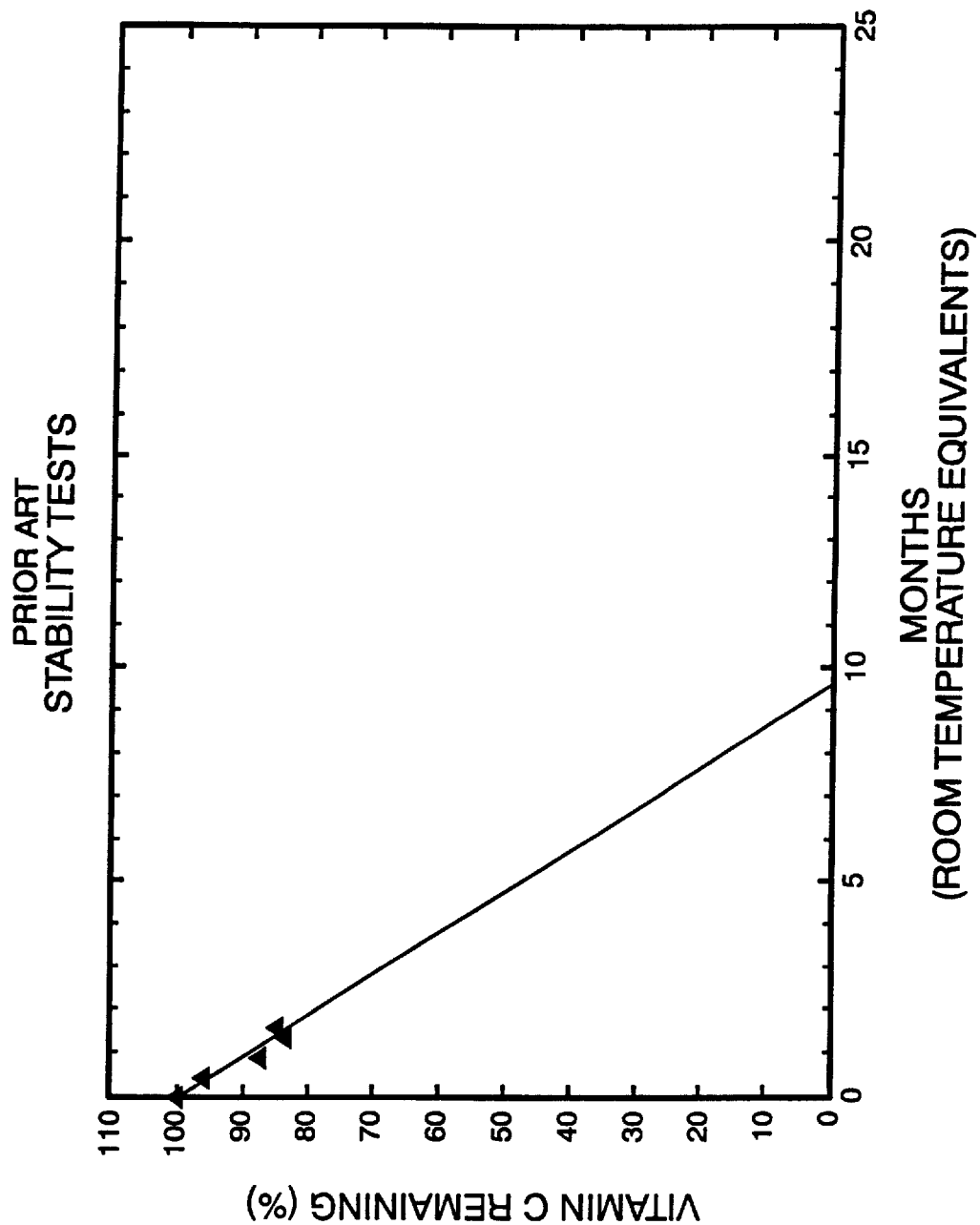
FIGS. 5a and 5b compare the stability of a typical commercially available liquid vitamin C composition (FIG. 5a) with the stability of the vitamin C concentrate compositions of the invention (FIG. 5b), which are prepared with and without an added aldonic component and with and without a zinc component.

FIG. 5a depicts the stability of a typical commercially-available liquid vitamin C composition based on U.S. Pat. No. 5,140,043 (Darr et al.).

Figure 5B:
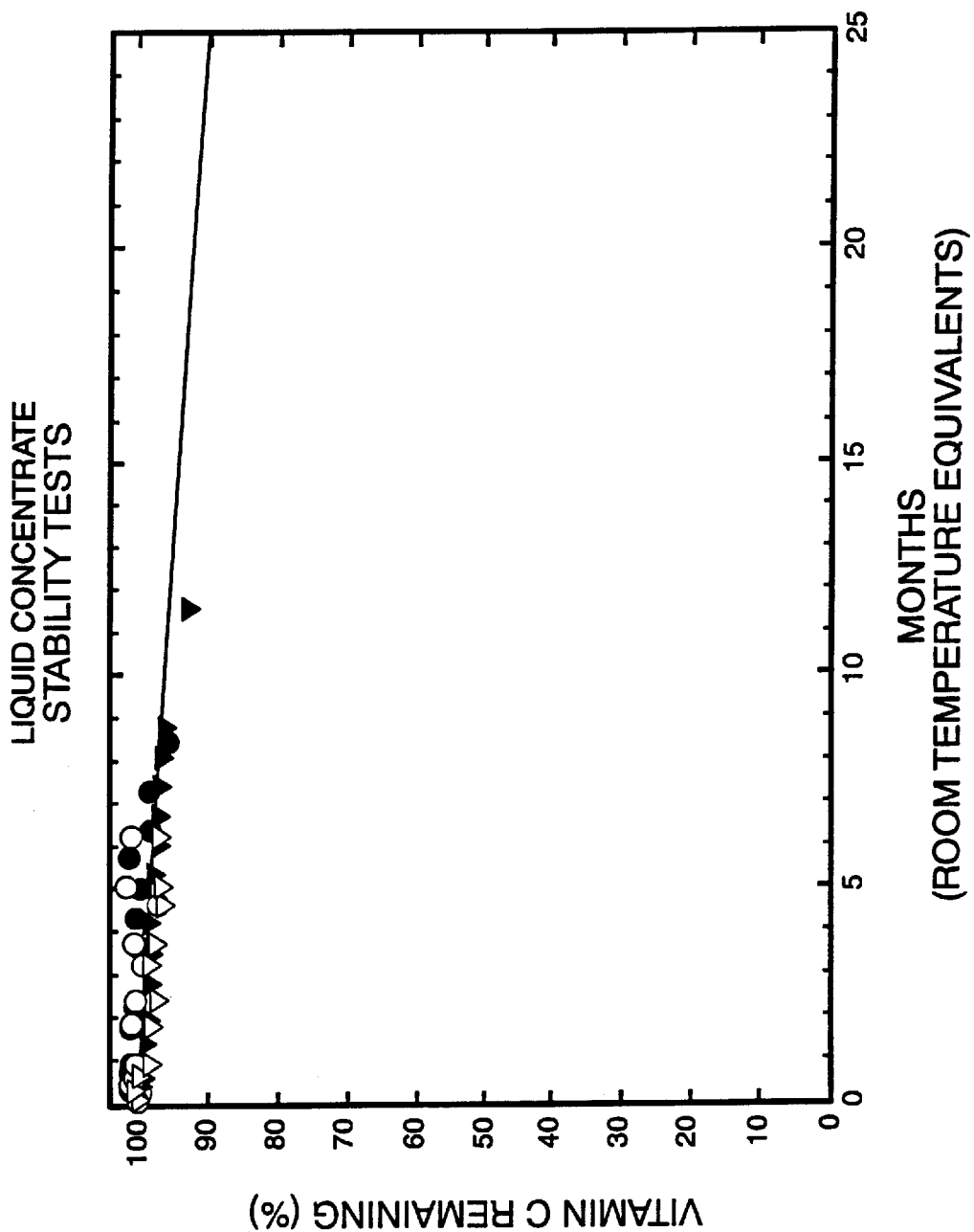

FIG. 5b depicts the superior stability of vitamin C in typical concentrate compositions of the invention, illustrating the comparable stabilities of four different mixtures having different ascorbate, aldonic, zinc and polyol compositions. These concentrate compositions vary with respect to concentration of ascorbate (10–15 wt. % Vitamin C as calcium ascorbate), the presence or absence of added aldonic compounds (threonate), and the presence or absence of other trace elements (zinc), and have varying ratios of the polyols in the solvent one employs (glycerol vs. 70% sorbitol).

The stability of each of these four compositions is assessed by sampling mixtures stored at either 22° C. (room temperature) or 40° C. (accelerated aging) and by measuring the remaining ascorbate by calorimetric procedures. Because chemical decomposition is accelerated by elevated temperature, the timescale of accelerated aging tests is adjusted to "room temperature" by an appropriate factor predicted by the Arrhenius equation. Various concentrate compositions of the invention retain greater than 90% of their original vitamin C potency for 25 months at room temperature (FIG. 5b). In contrast, a commercially available vitamin C liquid composition retains 90% of its original potency for only about one month (FIG. 5b).

Having described my invention in such terms as to enable those skilled in the art to understand and practice it and, having identified the presently preferred modes of the practice thereof, I claim:

1. A liquid vitamin C concentrate composition, comprising:
   (a) at least one mineral ascorbate; and
   (b) at least one pharmacologically acceptable liquid organic polyol solvent for said mineral ascorbate;
   said composition having a pH between about 5 and 7.

2. The liquid concentrate composition of claim 1, which also includes at least one aldonic compound.

3. A liquid vitamin C liquid concentrate composition, comprising the reaction product of a reaction mixture which includes:
   (a) at least one mineral ascorbate; and
   (b) at least one pharmacologically acceptable liquid organic polyol solvent for said mineral ascorbate;
   said concentrate composition having a pH about 5 and 7.

4. The liquid concentrate composition of claim 3, in which the reaction mixture includes an aldonic compound.

5. The liquid concentrate composition of claim 3, in which the reaction mixture includes a pharmacologically acceptable zinc compound.

6. The concentrate composition of claim 5 in which the zinc compound is a water-soluble zinc salt.

7. The concentrate composition of claim 6 in which the reaction mixture includes an aldonic compound.

8. A vitamin C product prepared from the concentrate composition of claim 1.

9. The method for application of vitamin C comprising introducing to the human body the vitamin C product of claim 8.

10. The reaction product of claim 3 which contains a compound characterized by the HPLC peak having an absorption maximum at about 285 nm and appearing after the solvent front peaks and before the ascorbate peaks.

11. The reaction product of claim 3 which contains 4-hydroxy-5-methyl-3(2H)-furanone.

12. The reaction product of claim 3 which contains 3-hydroxy-kojic acid.

13. The composition of claim 1 which contains 4-hydroxy-5-methyl-3(2H)-furanone.

14. The composition of claim 1 which contains 3-hydroxy-kojic-acid.

15. The product of claim 8 which contains 4-hydroxy-5-methyl-3(2H)-furanone.

16. The product of claim 8 which contains 3-hydroxy kojic acid.

* * * * *